United States Patent [19]

Mais et al.

[11] Patent Number: 4,948,886

[45] Date of Patent: Aug. 14, 1990

[54] PROCESS FOR THE PREPARATION OF BENZOTHIAZEPINONE DERIVATIVES

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 293,265

[22] Filed: Jan. 4, 1989

[30] Foreign Application Priority Data

Jan. 9, 1988 [DE] Fed. Rep. of Germany ....... 3800386

[51] Int. Cl.$^5$ .......................................... C07D 281/210
[52] U.S. Cl. .................................................. 540/491
[58] Field of Search ............................................ 540/491

[56] References Cited

U.S. PATENT DOCUMENTS 2,791,612  5/1957  Kinstler et al. ...................... 564/440
3,075,967  1/1963  Krapcho ............................... 540/491

FOREIGN PATENT DOCUMENTS 823738  12/1951  Fed. Rep. of Germany ...... 564/440
2141777   1/1973  France ................................. 564/440

OTHER PUBLICATIONS

Bulletin Des Societes Chimiques Belges, Band 60, 1951, Seiten 319–324, Osford, GB; J. Nys et al.: "Synthese et Caracterisation de l'o-amino-thiophenol" *Insgesamt, Insbesondere Seite 322, Beispiel 1*.

*Primary Examiner*—Robert T. Bond
*Attorney, Agent, or Firm*—Sprung, Horn, Kramer & Woods

[57] ABSTRACT

Benzothiazepinone derivatives can be prepared by alkaline hydrolysis of benzothiazoles to give o-amino-thiophenols, isolation thereof by acidification and further reaction with acrylic acids. In this connection, the acidification is carried out using a mineral acid, after which the o-amino-thiophenol is extracted using a water-insoluble solvent and is reacted in this extract with an acrylic acid.

20 Claims, No Drawings

PROCESS FOR THE PREPARATION OF BENZOTHIAZEPINONE DERIVATIVES

BACKGROUND OF THE INVENTION

The invention relates to a process for the preparation of benzothiazepinone derivatives from optionally substituted benzothiazoles which are first hydrolyzed to give o-amino-thiophenols and then reacted further with optionally substituted acrylic acids.

Benzothiazepinone derivatives are outstandingly suitable co-catalysts for controlling isomer ratios in nuclear chlorinations of alkylbenzenes in the presence of Friedel-Crafts catalysts.

It has been disclosed in U.S. Pat. No. 2,791,612 that the preparation of o-amino-thiophenol by alkaline hydrolysis of benzothiazole and subsequent acidification with mineral acid leads to by-products which in some cases enter into the reverse reaction to give benzothiazole; only unsatisfactory yields are therefore obtained even with careful maintenance of the reaction parameters. It is therefore proposed to work with acetic acid instead of with a mineral acid.

The reaction of optionally substituted o-amino-thiophenols with optionally substituted acrylic acids is disclosed in U.S. Pat. No. 3,075,967. For example, phenylcrotonic acid and o-amino-thiophenol are fused together at 160°–175° C. It is disadvantageous in this connection that these reactions in the melt lead to low yields (J. Chem. Soc. 130 (1927), 2738) and that in this connection not only benzothiazepinone derivatives but also isomeric benzothiazine derivatives are formed (Chem. Ber. 119 (1986), 3109).

The reaction of some substituted acrylic acids with o-amino-thiophenol in high-boiling, water-miscible solvents is furthermore known (Tetrahedron 42 (1986), 2731); in this connection, the benzothiazepinone derivatives can only be isolated by aqueous work-up.

SUMMARY OF THE INVENTION

A process for the preparation of benzothiazepinone derivatives of the formula

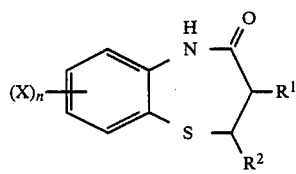
(I)

wherein
$R^1$ and $R^2$ independently of one another stand for hydrogen, $C_1$–$C_4$-alkyl or $(X)_n$-phenyl or together form $C_3$–$C_5$-alkylene,
X stands for hydrogen, $C_1$–$C_4$-alkyl or $C_1$–$C_4$-alkoxy and
n denotes 1 or 2,
by alkaline hydrolysis of benzothiazoles of the formula

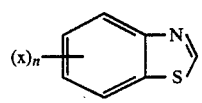
(II)

to give o-amino-thiophenols of the formula

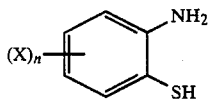
(III)

isolation thereof by acidification and reaction with acrylic acids of the formula $$R^2CH=CR^1-COOH \quad (IV)$$

wherein
$R^1$, $R^2$, X and n have the meaning mentioned, has now been found, which is characterized in that the acidification is carried out using a mineral acid, the mixture is then extracted using a water-insoluble solvent and the extract is reacted with the acrylic acid.

DETAILED DESCRIPTION OF THE INVENTION

The radicals $R^1$ and $R^2$ independently of one another denote hydrogen, $C_1$–$C_4$-alkyl, such as methyl, ethyl, propyl, isopropyl, butyl or isobutyl, or phenyl which is substituted once or twice with the substituents X described further below, and furthermore together denote $C_3$–$C_5$-alkylene, such as trimethylene, tetramethylene or pentamethylene. In a preferred manner, $R^1$ and $R^2$ independently of one another denote hydrogen, methyl or phenyl, and together denote the tetramethylene group. In a particularly preferred manner, one of the radicals $R^1$ and $R^2$ is hydrogen and the other is hydrogen, methyl or phenyl. The substituent X stands for hydrogen, $C_1$–$C_4$-alkyl, such as the abovementioned, or $C_1$–$C_4$-alkoxy, such as methoxy, ethoxy, propoxy, isopropoxy, butoxy or isobutoxy. In a preferred manner, the substituent X stands for hydrogen, methyl or methoxy, in a particularly preferred manner for hydrogen. The index n stands for the number 1 or 2, preferably for the number 1.

An example of the compounds of the formula (I) which are preparable according to the invention which may be mentioned by name are, where the system was numbered as follows:

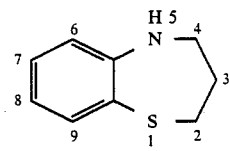

2,3-dihydro-1,5-benzothiazepin-4(5H)-one,
2,3-dihydro-2-methyl-1,5-benzothiazepin-4(5H)-one,
2,3-dihydro-3-methyl-1,5-benzothiazepin-4(5H)-one,
2,3-dihydro-7,8-dimethyl-1,5-benzothiazepin-4(5H)-one,
2,3-dihydro-7-methyl-1,5-benzothiazepin-4(5H)-one,
2,3-dihydro-2,3-dimethyl-1,5-benzothiazepin-4(5H)-one,
2,3-dihydro-2,3-tetramethylene-1,5-benzothiazepin-4(5H)-one,
2,3-dihydro-2-phenyl-1,5-benzothiazepin-4(5H)-one,
2,3-dihydro-7-methoxy-1,5-benzothiazepin-4(5H)-one.

The hydrolysis of the benzothiazoles of the formula (II) is carried out using aqueous alkaline solutions. In general, any compound can be employed for this which produces a sufficiently high concentration of OH-ions in aqueous solution. Preferably, solutions of alkali metal hydroxides, for example having a concentration of 20 to 60% by weight, preferably 30 to 50% by weight, particularly preferably 30 to 50% by weight, of NaOH solution are employed.

The hydrolysis takes place in a wide temperature range up to the boiling point of the mixture of the aqueous alkaline solution and benzothiazoles of the formula (II). Low temperatures in the range of room temperature are, in general, of little advantage because of the low reaction rate. Preferred temperatures are therefore from 50° C., preferably from 100° C., up to the boiling point of the hydrolysis mixture; working at reflux temperature is particularly preferred.

The alkaline hydrolysis mixture must be acidified to release the o-amino-thiophenols of the formula (III). According to the invention, any mineral acid is suitable for the acidification, for example nitric acid, sulphuric acid, hydrochloric acid or phosphoric acid, with or without dilution with water. The aqueous dilute form is preferred. A 30 to 70% by weight sulphuric acid or a 20 to 35% by weight hydrochloric acid is particularly preferred. For practical reasons, the concentration of the acid should advantageously be chosen so that the resulting salts do not precipitate from the aqueous phase and make the subsequent phase separation difficult. If desired, the mixture can be diluted with further water depending on the particular temperature until, for example, precipitated salts are dissolved again.

The temperature at which the neutralization with the mineral acid is carried out is in general any temperature up to the boiling point of the mixture. Neutralization is preferably carried out in a temperature range from 60° to 120° C., particularly preferably at 80° to 100° C.

The o-amino-thiophenol of the formula (III) forming on acidification is extracted by addition of a solvent. In principle, any water-insoluble solvent is suitable for this. Examples thereof are aliphatic hydrocarbons, aliphatic halogenated hydrocarbons, aromatic hydrocarbons, aromatic halogenated hydrocarbons, water-insoluble esters or water-insoluble ethers; in a preferred manner, aromatic hydrocarbons and aromatic halogenated hydrocarbons, in a particularly preferred manner aromatic halogenated hydrocarbons, are employed. Examples of such particularly preferred aromatic halogenated hydrocarbons are: chlorobenzene, bromobenzene, the isomeric dichlorobenzenes, the isomeric chlorotoluenes or the isomeric bromotoluenes.

The reaction of the extract of the o-amino-thiophenol of the formula (III) with the acrylic acid of the formula (IV) can be carried out without further purification of this extract. It is carried out in a wide temperature range from room temperature up to the boiling point of the reaction mixture. It is preferred to conduct the reaction initially in a range from 80° to 120° C. and then, if desired, to increase the temperature to the boiling point of the reaction mixture. In a preferred variant, the water of reaction is in this case removed from the reaction mixture with the extracting solvent by azeotropic distillation, the co-distilled extracting agent in this case being again fed back into the reaction mixture in a known manner after separation in a water separator. To this end, the reaction mixture can advantageously be heated under reflux until water no longer separates from the condensate.

On cooling the reaction mixture, the benzothiazepinone derivative of the formula (I) separates off. To this end, the reaction mixture is advantageously cooled to room temperature, but it is also possible to work at a slightly elevated temperature. The reaction product of the formula (I) precipitates out during the course of this in an already pure form and can be separated from the mother liquor by customary methods, for example by filtration or centrifugation. If necessary, the reaction product (I) separated off can be washed with the extracting solvent which was also the reaction medium.

The benzothiazepinone derivatives of the formula (I) are excellent co-catalysts, in addition to the customary Friedel-Crafts catalysts, for the nuclear chlorination of alkylbenzenes. These co-catalysts allow control of the ortho/para ratio. To this end, the benzothiazepinone derivatives can be employed in the solvent-moist form or alternatively after previous drying.

Obtaining and using the benzothiaze-pinone derivatives in solvent-moist form is the preferred and industrially most favoured variant. The extracting solvent/reaction medium chosen in each case ensues from the desired use of the benzothiazepinones: if they are to be employed, for example, for co-catalysis of nuclear chlorination of toluene, the particularly preferred solvent for extraction (later the reaction medium) is toluene, a chlorotoluene or a chlorotoluene mixture, preferably a chlorotoluene mixture. However, if it is intended to employ the benzothiazepinones, for example, for the co-catalysis of nuclear chlorinations of cumene, cumene, chlorocumene and/or a chlorocumene mixture, preferably a chlorocumene mixture, is used as the extracting solvent.

It is surprising that, in contrast to the teaching of U.S. Pat. No. 2,791,612, the o-amino-thiophenols can be isolated by the process according to the invention in pure form and high yield by acidification with mineral acid. The increase in the yields of the benzothiazepinone derivatives by the use of the extracting solvents mentioned is likewise surprising. The simplicity of the isolation of the benzothiazepinone derivatives from the mother liquors is very advantageous industrially. The employment of the benzothiazepinone derivatives as co-catalysts in the nuclear chlorination of alkylaromatics without previous drying is also an advantage of the process according to the invention.

The following examples are intended to illustrate the process according to the invention without, however, limiting it to these examples.

EXAMPLE 1

2,3-Dihydro-1,5-benzothiazepin-4(5H)-one 100 parts by weight of 50% NaOH solution were initially introduced and heated to reflux. 66 parts by weight of benzothiazole were added in the course of 3 hours and the mixture was then stirred under reflux for 2 h. It was then cooled somewhat and acidified at 100° C. with 120 parts by weight of conc. HCl and a further 100 parts by weight of water were then added. 70 parts by weight of a chlorotoluene mixture comprising about 50% o-chlorotoluene and about 50% p-chlorotoluene were added and the separating water phase was separated off. The organic phase was heated to 100° C., 35 parts by weight of acrylic acid were added in the course of 1 hour and the mixture was heated to reflux until water no longer separated from the condensate. The organic phase of the condensate was fed back into the reaction mixture. The mixture was then cooled to about 25° C. and the solid was filtered off with suction. It was washed with 70 parts by weight of the chlorotoluene mixture.

The product was dried in order to determine the yield.

Weight: 71 parts by weight=81% of theory; Melting point: 216°-218° C.

EXAMPLE 2

2,3-Dihydro-2-methyl-1,5-benzothiazepin-4(5H)-one

The procedure was as in Example 1, only 42 parts by weight of methacrylic acid were added here instead of the acrylic acid.

After drying, a weight of 61.5 parts by weight=65% of theory was obtained:

Melting point: 176°-177° C.

EXAMPLE 3

2,3-Dihydro-3-methyl-1,5-benzothiazepin-4(5H)-one

The procedure was initially as in Example 1. The mixture was then acidified at 100° to 110° C. with 70 parts by weight of about 50% strength sulphuric acid and 150 parts by weight of water and then 70 parts by weight of the chlorotoluene mixture were added. After separating off the aqueous phase, the organic phase was heated to 100° C. and 42 parts by weight of liquid crotonic acid were added in the course of 1 h. After the addition, the mixture was heated under reflux until completion of the separation of water, then cooled to about 30° C., filtered off with suction and washed with 80 parts by weight of the chlorotoluene mixture.

The product was dried in order to determine the yield.

Weight: 85.5 parts by weight=90.5% of theory; Melting point: 206°-207° C.

EXAMPLE 4

2,3-Dihydro-2-phenyl-1,5-benzothiazepin-4(5H)-one

The procedure was as in Example 3, only 72 parts by weight of cinnamic acid, mixed with 72 parts by weight of chlorotoluene mixture, were added in liquid form instead of the crotonic acid.

After drying, a weight of 96 parts by weight=77% of theory was obtained; Melting point: 175°-176° C.

EXAMPLE 5-7

In an analogous manner to the previous examples, 2,3-dihydro-3-propyl-1,5-benzothiazepin-4(5H)-one (melting point: 120°-122° C.) was obtained from benzothiazole and 2-hexenic acid, 2,3-dihydro-2,3-tetramethylene-1,5-benzothiazepin-4(5H)-one (melting point: 225°-227° C.) was obtained from benzothiazole and cyclohexene-1-carboxylic acid and 2,3-dihydro-7,8-dimethyl-1,5-benzothiazepin-(5H)one (melting point: 241°-244° C.) was obtained from 5,6-dimethylbenzothiazole and acrylic acid.

USE EXAMPLE 8

A solution of 100 parts by weight of toluene, 0.0175 part by weight of FeCl$_3$ and 0.004 part by weight of the compound of the formula

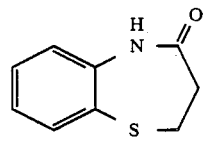

(2,3-dihydro-1,5-benzothiazepin-4(5)-one)

was prepared. This solution was added to a continuously working chlorination reactor at 40°-43° C., the equivalent amount of chlorination mixture being simultaneously removed. Gaseous chlorine was added rapidly in such a way that the conversion was about constant at 90 mol-%. The reaction mixture removed contained about 7.1% by weight of toluene and the ratio of ortho-chlorotoluene to para-chlorotoluene was o/p=0.70.

USE EXAMPLE 9

The process of Example 8 was repeated. However, 0.005 part by weight of the compound of the formula

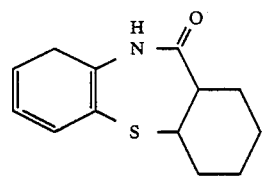

(2,3-dihydro-2,3-tetra-methylene-1,5-benzothiazepin-4(5H)-one)

was added. The cooled reaction mixture contained about 7.0% by weight of toluene and the ratio of ortho-chlorotoluene to para-chlorotoluene was o/p=0.64.

What is claimed is:

1. A process for the preparation of benzothiazepinone derivatives of the formula

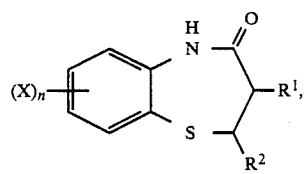

wherein $R^1$ and $R^2$ independently of one another stand for hydrogen, $C_1$-$C_4$-alkyl or $(X)_n$-phenyl or together form $C_3$-$C_5$-alkylene, X stands for hydrogen, $C_1$-$C_4$-alkyl or $C_1$-$C_4$alkoxy and n denotes 1 or 2, by alkaline hydrolysis of benzothiazoles of the formula

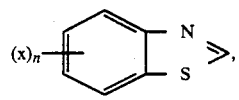

to give o-amino-thiophenols of the formula

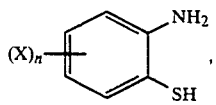

isolation thereof by acidification and reaction with acrylic acids of the formula $$R^2CH=CR^1-COOH$$

wherein

R¹, R², X and n have the meaning mentioned, characterized in that the acidification is carried out using a mineral acid, the mixture is then extracted using a water-insoluble solvent and the extract is reacted with the acrylic acid.

2. The process according to claim 1, characterized in that nitric acid, sulphuric acid, hydrochloric acid or phosphoric acid, with or without dilution with water are employed as the mineral acid.

3. The process according to claim 2, characterized in that aqueous dilute mineral acids are employed.

4. The process according to claim 1, characterized in that aromatic hydrocarbons and aromatic halogenated hydrocarbons are employed as the extracting solvent.

5. The process according to claim 4, characterized in that aromatic halogenated hydrocarbons are employed as the extracting solvent.

6. The process according to claim 5, characterized in that, for later use of the benzothiazepinone derivatives in the nuclear chlorination of toluene, chlorotoluene is employed as the extracting solvent.

7. The process according to claim 1, characterized in that the reaction of the o-amino-thiophenols with the acrylic acids is carried out with the exclusion of water.

8. The process according to claim 7, characterized in that the reaction temperature is increased up to the boiling temperature of the reaction mixture whereby the water of reaction is removed by azeotropic distillation with the aid of the extracting solvent.

9. The process according to claim 1, characterized in that the benzothiazepinone derivatives are isolated from the reaction solution by crystallization.

10. The process according to claim 9, characterized in that the benzothiazepinone derivatives are isolated as a solvent-moist crystallizate.

11. The process according to claim 1, characterized in that 2,3-dihydro-1,5-benzothiazepin-4(5H)-one is obtained as benzothiazepinone derivative.

12. The process according to claim 1, characterized in that the radicals R¹ and R² independently of one another denote hydrogen, methyl or phenyl, and together denote the tetramethylene group.

13. The process according to claim 12, characterized in that one of the radicals R¹ and R² is hydrogen and the other is hydrogen, methyl or phenyl.

14. The process according to claim 1, characterized in that the substituent X stands for hydrogen, methyl or methoxy.

15. The process according to claim 14, characterized in that the substituent X stands for hydrogen.

16. The process according to claim 1, characterized in that the index n stands for the number 1.

17. The process according to claim 1, characterized in that the hydrolysis is carried out with aqueous NaOH solution of 20-60% strength by weight.

18. The process according to claim 1, characterized in that the hydrolysis is carried out at a temperature of from 50° C. to the boiling point of the hydrolysis mixture.

19. The process according to claim 18, characterized in that the hydrolysis is carried out at reflux temperature.

20. The process according to claim 1, characterized in that the acidification with the mineral acid is carried out at any temperature up to the boiling point of the mixture.

* * * * *